United States Patent [19]

Lang et al.

[11] Patent Number: 4,956,174
[45] Date of Patent: * Sep. 11, 1990

[54] COMPOSITIONS FOR COLORING THE SKIN BASED ON INDOLE DERIVATIVES

[75] Inventors: Gerard Lang, Saint-Gratien; Herve Richard; Madeleine Leduc, both of Paris; Alex Junino, Livry-Gargan, all of France

[73] Assignee: L'Oreal, Paris, France

[*] Notice: The portion of the term of this patent subsequent to Apr. 18, 2006 has been disclaimed.

[21] Appl. No.: 21,931

[22] Filed: Mar. 5, 1987

[30] Foreign Application Priority Data

Mar. 6, 1986 [LU] Luxembourg ............................ 86347

[51] Int. Cl.$^5$ .............................................. A61K 7/42
[52] U.S. Cl. ...................................... 424/63; 514/415
[58] Field of Search .................. 424/63; 514/411, 415; 548/414, 430, 469, 492, 493, 494

[56] References Cited

U.S. PATENT DOCUMENTS

| | | | |
|---|---|---|---|
| 3,194,734 | 7/1965 | Seemuller et al. | 548/469 X |
| 3,467,670 | 9/1968 | Suh | 548/506 |
| 3,838,167 | 9/1974 | Jones | 548/493 X |
| 3,976,639 | 8/1976 | Batcho et al. | 546/232 |
| 4,013,404 | 3/1977 | Parent et al. | 8/423 |
| 4,021,538 | 5/1977 | Yu et al. | 424/63 X |
| 4,208,183 | 6/1980 | Grollier et al. | 8/409 |
| 4,515,773 | 5/1985 | Herlihy | 424/59 |
| 4,522,808 | 6/1985 | Jacquet et al. | 424/59 |
| 4,776,857 | 10/1988 | Carroll et al. | 424/63 X |

FOREIGN PATENT DOCUMENTS

| | | | |
|---|---|---|---|
| 239826 | 10/1987 | European Pat. Off. | |
| 2187456 | 9/1987 | United Kingdom | 548/414 |
| 82/00032 | 1/1982 | World Int. Prop. O. | 548/469 |

OTHER PUBLICATIONS

Chemical Abstracts, vol. 75, 1971, p. 209, No. 118189v, Merchant et al.

Primary Examiner—Ellis P. Robinson
Assistant Examiner—Susan S. Rucker
Attorney, Agent, or Firm—Cushman, Darby & Cushman

[57] ABSTRACT

Cosmetic composition designed to impart to the skin a coloring which is substantially similar to the pigmentation resulting from natural tanning, characterized in that it contains, in a cosmetically acceptable medium suitable for topical application, at least one compound of the formula:

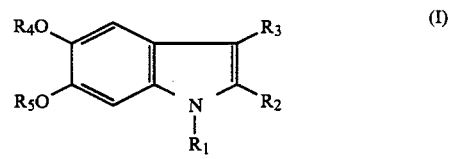

in which $R_1$ denotes a hydrogen atom, a lower alkyl group or a residue —$SiR_9R_{10}R_{11}$, $R_2$ and $R_3$, which may be identical or different, denote a hydrogen atom, a lower alkyl group, a carboxyl group, a lower alkoxycarbonyl group or a group —$COOSiR_9R_{10}R_{11}$; $R_4$ and $R_5$ which may be identical or different, denote a hydrogen atom, a linear or branched $C_1$–$C_{20}$ alkyl group, a formyl group, a linear or branched $C_2$–$C_{20}$ acyl group, a linear or branched $C_3$–$C_{20}$ alkenoyl group, a group $R_6OSO_2$—, a group —$SiR_9R_{10}R_{11}$, a group —$P(O)(OR_6)_2$ or an aralkyl group, or alternatively $R_4$ and $R_5$, with the oxygen atoms to which they are attached, form a ring optionally containing a carbonyl group when at least one of the groups, $R_1$, $R_2$ or $R_3$ is other than hydrogen or alternatively a thiocarbonyl group, a residue $>P(O)OR_6$, a group $>CR_7R_8$ or a methylene group, $R_6$ denoting a hydrogen atom or a lower alkyl group, $R_7$ denoting a hydrogen atom or a lower alkyl group, $R_8$ denoting a lower alkoxy group or a mono- or dialkylamino group and $R_9$, $R_{10}$ or $R_{11}$, which may be identical or different, denoting linear or branched lower alkyl groups, at least one of the substituents $R_1$, $R_2$, $R_3$, $R_4$ and $R_5$ being other than hydrogen; and the corresponding salts with alkali metals, alkaline earth metals, ammonium or amines.

11 Claims, No Drawings

COMPOSITIONS FOR COLORING THE SKIN BASED ON INDOLE DERIVATIVES

The present invention relates to new cosmetic compositions designed to impart to the skin a coloring which is substantially similar to the pigmentation resulting from natural tanning.

Natural tanning is due to the melanization which results from the exposure of the human epidermis to light radiation having a wavelength of between 280 and 400 nanometers.

Compositions designed to impart an artificial tan to the skin have already been proposed in the past, and compositions based on dihydroxyacetone may be mentioned in particular. The tanning obtained by means of dihydroxyacetone results from a reaction between the active product and the protein components of the skin, independently of an exposure to the sun.

The application of such compounds has, however, a disadvantage which results from the mechanism responsible for the appearance of coloring, and different shades are very frequently obtained after successive applications, according to whether or not the skin has cornified portions. Moreover, the coloring obtained is removed in an irregular manner on washing, thereby leading to shade differences. Moreover, the melanoidins developed do not give protection against solar radiation.

The applicants have discovered that a coloring of the skin resembling the pigmentation which results from natural tanning could be developed by means of indole derivatives. This coloring is due to their conversion, with or without activation by solar radiation, to a pigment resembling the natural pigment responsible for tanning. The appearance of this coloring may be activated, in particular, by ultraviolet radiation.

A subject of the invention hence consists of new compositions for coloring the skin based on indole derivatives.

Another subject of the invention consists of the process for coloring the skin employing these compounds.

Other subjects of the invention will emerge on reading the description and the examples which follow.

The compositions according to the invention, designed to be used for coloring the skin, are essentially characterized in that they contain, in a cosmetically acceptable medium suitable for topical application, at least one compound of formula:

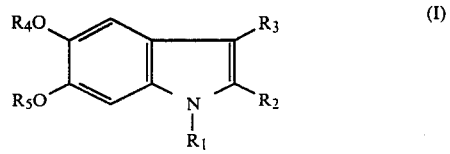

in which $R_1$ denotes a hydrogen atom, a lower alkyl group or a residue $—SiR_9R_{10}R_{11}$, $R_2$ and $R_3$, which may be identical or different, denote a hydrogen atom, a lower alkyl group, a carboxyl group, a lower alkoxycarbonyl group or a group $—COOSiR_9R_{10}R_{11}$; $R_4$ and $R_5$ which may be identical or different, denote a hydrogen atom, a linear or branched $C_1$-$C_{20}$ alkyl group, a formyl group, a linear or branched $C_2$-$C_{20}$ acyl group, a linear or branched $C_3$-$C_{20}$ alkenoyl group, a group $R_6OSO_2—$, a group $—SiR_9R_{10}R_{11}$, a group $—P(O)(OR_6)_2$ or an aralkyl group, or alternatively $R_4$ and $R_5$, with the oxygen atoms to which they are attached, form a ring optionally containing a carbonyl group when at least one of the groups $R_1$, $R_2$ or $R_3$ is other than hydrogen or alternatively a thiocarbonyl group, a residue $>P(O)OR_6$, a group $>CR_7R_8$ or a methylene group, $R_6$ denoting a hydrogen atom or a lower alkyl group, $R_7$ denoting a hydrogen atom or a lower alkyl group, $R_8$ denoting a lower alkoxy group or a mono- or dialkylamino group and $R_9$, $R_{10}$ or $R_{11}$, which may be identical or different, denoting linear or branched lower alkyl groups, at least one of the substituents $R_1$, $R_2$, $R_3$, $R_4$ and $R_5$ being other than hydrogen; and the corresponding salts with alkali metals, alkaline earth metals, ammonium, or amines.

In the groups defined above, a lower alkyl or lower alkoxy group preferably denotes a group having 1 to 6 carbon atoms.

Among the compounds of formula (I), there may be mentioned the following compounds which appear in Table I.

TABLE I

| No. | Name of compound | Melting point and boiling point (b.p.) °C. |
|---|---|---|
| 1 | 5,6-Dibenzyloxyindole | 114° |
| 2 | 5-Benzyloxy-6-methoxyindole | 95-6° |
| 3 | 6-Benzyloxy-5-methoxyindole | 148° |
| 4 | 6-Hydroxy-5-methoxyindole | 111° |
| 5 | 5-Hydroxy-6-methoxyindole | 116° |
| 6 | 5,6-Diacetoxyindole | 140° |
| 7 | 6-Acetoxy-5-methoxyindole | 140° |
| 8 | (5 or 6)-Acetoxy-(6 or 5)-hydroxyindole | 184° |
| 9 | 5,6-Dibenzyloxy-2-carbethoxyindole | 140° |
| 10 | 5,6-Dibenzyloxy-2-carboxyindole | 201-2° |
| 11 | 5,6-Dihydroxy-2-carbethoxyindole | 194° |
| 12 | 5,6-Dihydroxy-2-carboxyindole | 240° (d) |
| 13 | 5,6-dibenzyloxy-2-methylindole | 116° |
| 14 | 5,6-Dihydroxy-2-methylindole | 216-8° |
| 15 | 5,6-Dibenzyloxy-3-methylindole | 114° |
| 16 | 5,6-Dihydroxy-3-methylindole | 156° |
| 17 | (5 or 6)-Formyloxy-(6 or 5)-hydroxyindole | 161° |
| 18 | (5 or 6)-Acetoxy-(6 or 5)-formyloxyindole | — |
| 19 | 6-Formyloxy-5-methoxyindole | 118° |
| 20 | 6-Benzyloxy-5-butoxyindole | 116° |
| 21 | 5-Butoxy-6-hydroxyindole | 91° |
| 22 | 5-Benzyloxy-6-butoxyindole | |
| 23 | 6-Butoxy-5-hydroxyindole | 105° |
| 24 | (5 or 6)-Hydroxy-(6 or 5)-trimethylsilyl- | 97° |

TABLE I-continued

| No. | Name of compound | Melting point and boiling point (b.p.) °C. |
|---|---|---|
| | oxyindole | |
| 25 | 5,6-Bis(trimethylsilyloxy)indole | 67° *b.p. 151° |
| 26 | 5,6-[(1-Ethoxyethylidene)dioxy]indole | 69° *b.p. 160° |
| 27 | 5,6-Dihydroxyindole cyclic phosphodiester | >260° |
| 28 | 5,6-Thiocarbonyldioxyindole | >260° |
| 29 | 5-Methoxy-6-trimethylsilyloxyindole | 90–1° |
| 30 | 5,6-Bis(trimethylsilyloxy)-2-methylindole | 99° |
| 31 | 5,6-Carbonyldioxy-2-methylindole | 143° |
| 32 | (5 or 6)-Hydroxy-(6 or 5)-myristoyloxyindole | 125–126° |
| 33 | 5,6-Dimyristoyloxyindole | 92° |
| 34 | (5 or 6)-Hydroxy-(6 or 5)-oleoyloxyindole | 94–100° |
| 35 | 5,6-Dioleoyloxyindole | 38–40° |
| 36 | 5,6-Bis(trimethylsilyloxy)-2-carbethoxyindole | 143° |
| 37 | 5,6-Bis(trimethylsilyloxy)-2-(trimethylsilyloxycarbonyl)indole | 173° |
| 38 | 5,6-Bis(trimethylsilyloxy)-3-methylindole | 84° |
| 39 | 6-Hexadecyloxy-5-methoxyindole | 68.5° |
| 40 | 6-Hexadecyloxy-5-hydroxyindole | 80° |
| 41 | 5-Hexadecyloxy-6-hydroxyindole | 79° |
| 42 | 5,6-Dipivaloyloxyindole | 139° |
| 43 | (5 or 6)-Hydroxy-(6 or 5)-pivaloyloxyindole | 130° |
| 44 | 5,6-Dihexanoyloxyindole | 60–63° |
| 45 | (5 or 6)-Hexanoyloxy-(6 or 5)-hydroxyindole | 88° |
| 46 | 5,6-Dibutanoyloxyindole | 74° |
| 47 | (5 or 6)-Butanoyloxy-(6 or 5)-hydroxyindole | 121° |

*at $1.06 \times 10^2$ Pa

The compounds according to the invention which are more especially preferred correspond to the formula I in which $R_1$ denotes hydrogen, $R_2$ and $R_3$, which may be identical or different, denote a hydrogen atom or a lower alkyl group, at least one of the substituents $R_4$ or $R_5$ denotes a linear or branched $C_1$–$C_{20}$ alkyl group or a linear or branched $C_2$–$C_{20}$ acyl group or a linear or branched $C_3$–$C_{20}$ alkenoyl group, the other denoting hydrogen, or alternatively $R_4$ and $R_5$ simultaneously denotes $SiR_9R_{10}R_{11}$ where $R_9$, $R_{10}$, $R_{11}$ have the meanings stated above.

The compounds of formula (I) are preferably present in compositions according to the invention in proportions of between 0.01 and 15% by weight relative to the total weight of the composition.

The appropriate cosmetic medium for application on the skin is either aqueous or anhydrous. It can contain one or more solvents which are acceptable from the cosmetic standpoint. Among these solvents, there may mentioned, by way of examples, $C_1$–$C_4$ lower alcohols such as ethanol, isopropanol or tert-butanol, ethylene glycol, propylene glycol, dipropylene glycol and tripropylene glycol, ethylene glycol monomethyl, monoethyl and monobutyl ethers and ethylene glycol monoethyl ether acetate.

The compositions according to the invention can take the form of lotions, oils, gels, emulsions, creams, milks, sticks or balms.

The lotions can be aqueous-alcoholic lotions or oleoalcoholic lotions based on lower alcohols such as ethanol or glycol such as propylene glycol and fatty acid esters such as isopropyl myristate.

The appropriate cosmetic medium is preferably in anhydrous form. An anhydrous medium, in the sense used in the invention, refers to a medium containing less than 1% of water.

The cosmetic medium according to the invention can also contain or consist exclusively of fats, which can be chosen from mineral oils such as liquid paraffin; animal oils such as whale oil, seal oil, menhaden oil, halibut liver oil, cod oil, tuna oil, turtle oil, tallow oil, neat's-foot oil, horse's-foot oil, sheep's-foot oil, mink oil, otter oil, marmot oil, and the like; and vegetable oils such as almond oil, groundnut oil, rapeseed oil, wheatgerm oil, olive oil, corn oil, jojoba oil, sesame oil, sunflower oil, palm-olive oil, walnut oil or similar oils.

Among fats, there may also be mentioned vaseline, paraffin wax, hydrogenated lanolin, acetylated lanolin and silicone oils. The waxes which can be used can be, inter alia, sipol wax, lanolin wax, beeswax, candelilla wax, microcrystalline wax, carnauba wax, spermaceti wax, cocoa butter, shea butter, silicone waxes, hydrogenated oils which are solid at 25° C., sugar glycerides, oleates, myristates, linoleates and calcium, magnesium, zirconium or aluminium stearates. Fatty alcohols can be used in such compositions and are, inter alia, lauryl, cetyl, myristyl, stearyl, palmityl and oleyl alcohols, optionally polyoxyethylenated or polyglycerolated. By way of polyoxyethylenated fatty alcohols lauryl, cetyl, stearyl and oleyl alcohols containing from 2 to 20 moles of ethylene oxide may be mentioned.

The compositions according to the invention can naturally contain cosmetic additives customarily used in this type of composition, such as thickeners, demulcents, humectants, superfatting agents, sequestering agents, emollients, wetting agents, surfactants, polymers, preservatives, antifoams, perfumes, emulsifiers, bactericides or any other ingredient customarily used in cosmetics.

The embodiments which are especially preferred consist of anhydrous oil and sticks.

The compositions according to the invention can be used for the protection or maintenance of a tan, and can contain, in addition to the compound of formula (I), sunscreens which are specific for UV-B radiation and/or UV-A radiation and compatible with the compounds according to the invention. It is hence possible to obtain a composition which screens the whole of the UV-B and UV-A radiation or only one of these fractions of radiation, while effecting a coloring of the skin which is similar to the pigmentation resulting from natural tanning.

The subject of the invention is also a process for coloring the skin similarly to the pigmentation which results from natural tanning and employing a compound corresponding to the formula I.

Some of the compounds according to the invention are known per se, while others are new. The new compounds correspond to the formula:

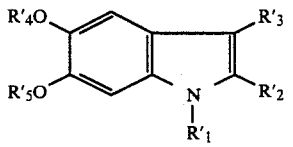

in which $R'_1$ denotes a hydrogen atom or a lower alkyl group; $R'_2$ and $R'_3$, which may be identical or different, denote a hydrogen atom, a lower alkyl group, a carboxyl group, a lower alkoxycarbonyl group or a —COOSi(CH$_3$)$_3$ group; $R'_4$ and $R'_5$, which may be identical or different, can denote a linear or branched $C_9$–$C_{20}$ alkyl group, a linear or branched $C_{10}$–$C_{20}$ acyl group, a linear or branched $C_3$–$C_{20}$ alkenoyl group or a group —P(O)(OR$_6$)$_2$, the other group $R'_4$ or $R'_5$ being able to be a hydrogen atom, a $C_1$–$C_8$ alkyl group, a formyl group, a $C_2$–$C_9$ acyl group or an aralkyl group;

$R'_4$ or $R'_5$ being able to denote a —Si(CH$_3$)$_3$ group when $R'_1$ is other than methyl; or alternatively $R'_4$ and $R'_5$ form, together with the oxygen atoms to which they are attached, a ring optionally containing a carbonyl group when one of the substituents $R'_1$, $R'_2$ or $R'_3$ is other than hydrogen, a thiocarbonyl group, a group >P(O)OR$_6$ or >CR$_7$R$_8$, R$_6$ denoting a hydrogen atom or a lower alkyl radical, R$_7$ denoting a hydrogen atom or a lower alkyl group, and R$_8$ denoting a lower alkoxy group or a mono- or dialkylamino group, and the corresponding salts with alkali metals, alkaline earth metals or amines.

The products according to the invention can be prepared according to processes which are known per se. The 5,6-dihydroxyindole derivatives, substituted or unsubstituted at the 2- and/or 3-positions, can be synthesized from compounds already substituted at the 5- and 6-positions, the final stage of formation being a reductive cyclization of a ,2-dinitrostyrene:

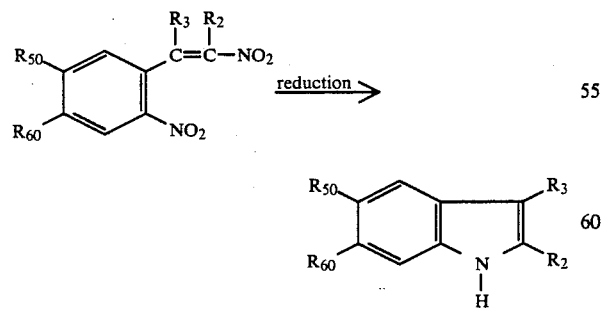

or alternatively the 5,6-dihydroxyindole derivatives substituted at the 1-, 2- and/or 3-positions can be synthesized from 5,6-dihydroxyindoles substituted at the 1-, 2- and/or 3-positions, by methods in which the presence of free bases in the reaction medium is avoided on account of the instability in basic medium of 5,6-dihydroxyindoles substituted at the 1-, 2- and/or 3-position.

Thus, it is possible to work either by phase transfer, in the case of the etherifications (such as for the compounds 39, 40 and 41), or by transesterification methods in the case of the 5,6-dihydroxyindole esters substituted at the 1-, 2- and/or 3-positions (such as for the compounds 27, 28 and 31-35). In these latter cases, the monoacyl and diacyl derivatives are separated by column chromatography.

The examples which follow are intended to illustrate the compounds and compositions according to the invention without being limiting in nature.

The absorption spectra of some compounds according to the invention are presented in Table II, the numbers refering to those which appear in Table I.

TABLE II

| No. | Solvent | λ max (ε max) |
|---|---|---|
| 3 | Ethanol | 295 nm (7180) |
|  |  | 272 nm (5120) |
| 4 | Propylene glycol | 300 nm (5360) |
|  |  | 275 nm (3780) |
|  |  | 230 nm (4590) |
| 5 | Propylene glycol | 300 nm (4020) |
|  |  | 282 nm (shld.) |
|  |  | 275 nm (4750) |
|  |  | 230 nm (6800) |
| 6 | Ethanol | 283 nm (6500) |
| 8 | Ethanol | 296 nm (6500) |
|  |  | 274 nm (4920) |
| 19 | Propylene glycol | 296 nm (5120) |
|  |  | 288 nm (4800) |
|  |  | 228 nm (7320) |
| 21 | Ethanol | 302 nm (3960) |
|  |  | 274 nm (2950) |
| 23 | Ethanol | 301 nm (6010) |
|  |  | 274 nm (3990) |
| 25 | Ethanol | 300 nm (3800) |
|  |  | 276 nm (shld. 2950) |
| 26 | Ethanol | 305 nm (6480) |
|  |  | 274 nm (3750) |
| 28 | Ethanol | 312 nm (24100) |
|  |  | 263 nm (8750) |
| 29 | Ethanol | 298 nm (6100) |
|  |  | 274 nm (4400) |
| 30 | Ethanol | 300 nm (8300) |
|  |  | 275 nm (5520) |
| 31 | Ethanol | 301 nm (8170) |
|  |  | 278 nm (shld. 5370) |
|  |  | 219 nm (20900) |
| 32 | Ethanol | 296 nm (6500) |
|  |  | 273 nm (4860) |
| 33 | Ethanol | 284 nm (6870) |
|  |  | 220 nm (29500) |
| 34 | Ethanol | 296 nm (6730) |
|  |  | 273 nm (5050) |
| 35 | Ethanol | 284 nm (7000) |
| 36 | Ethanol | 317 nm (22000) |
| 39 | Ethanol | 297 nm (5800) |
|  |  | 273 nm (3900) |
| 40 | Ethanol | 300 nm (5990) |
|  |  | 273 nm (4000) |
| 41 | Ethanol | 300 nm (6500) |
|  |  | 273 nm (4170) |
| 42 | Ethanol | 284 nm (6900) |
| 43 | Ethanol | 295 nm (6340) |
|  |  | 273 nm (4700) |
| 44 | Ethanol | 284 nm (7100) |
| 45 | Ethanol | 295 nm (6400) |
|  |  | 273 nm (4910) |
| 46 | Ethanol | 284 nm (6600) |
| 47 | Ethanol | 295 nm (6400) |
|  |  | 273 nm (4880) |

(shld. = shoulder)

PREPARATION EXAMPLES

Example I

Preparation of the compound No. 17 of Table I
(5-Formyloxy-6-hydroxyindole and
6-formyloxy-5-hydroxyindole)

2.39 g (0.0257 mole) of acetic formic anhydride are added dropwise at −5° C. to 1.8 g (0.0122 mole) of 5,6-dihydroxyindole dissolvd in 20 ml of dry ether. In the course of 6 hours, the temperature is raised gradually to 20° C. The mixture is left overnight with stirring. A white precipitate is collected which is filtered off and recrystallized in a toluene/acetone (3:2) mixture. The compound 17 is obtained (218 mg; yield: 10%) in the form of a white powder. The compound 17 is a 60:40 mixture of the two formyl derivatives, as shown by the proton NMR spectrum. MS (70 eV) for $C_9H_7NO_3$: 177($M^+$, 58%) 149(100), 120(17), 103(45) and 65(21).

Example II

Preparation of the compound No. 18 of Table I
(6-acetoxy-5-formyloxyindole and
5-acetoxy-6-formyloxyindole)

The above derivative 17 (150 mg; $8.5 \times 10^{-4}$ mole) is stirred for 4 hours with 2.25 ml of acetic anhydride and 0.12 ml of pyridine. After evaporation of the solvents, taking up in dichloromethane, successive washes with 0.1N aqueous HCl and 2% strength aqueous $NaHCO_3$ solutions and water, and drying, the derivative 18 is obtained (150 mg; yield: 80%) which, from the NMR spectrum is a 60:40 mixture of the two isomers.

Example III

Preparation of the compound No. 19 of Table I
(6-Formyloxy-5-methoxyindole)

A solution of 12 g (0.0735 mole) of 6-hydroxy-5-methoxyindole and 12.95 g (0.147 mole) of acetic formic anhydride in 100 ml of toluene is brought to reflux for 16 hours under nitrogen. After the mixture is cooled, 30 g of silica 60 are added to the reaction medium, the mixture is filtered and the filtrate concentrated twofold. The white precipitate obtained is filtered off and then recrystallized again in 30 ml of toluene. After being dried under vacuum, 4.2 g of the derivative 19 (white powder, 30% yield) are obtained.

Analysis: $C_{10}H_9NO_3$ Calculated: C 62.82; H 4.74; N 7.33. Found: C 62.84; H 4.75; N 7.29.

Example IV

Preparation of the compound No. 25 of Table I
[5,6-Bis(trimethylsilyloxy)indole]

0.3 g (0.002 mole) of 5,6-dihydroxyindole is added to 0.81 g (0.004 mole) of N,O-bis(trimethylsilyl)acetamide while stirring at room temperature. When the dissolution is complete, 2 ml of dichloromethane are added and this solution is passed through a column of silica 60, eluting with dichloromethane. The first fraction obtained is concentrated in a rotary evaporator and then dried under vacuum. 0.42 g (yield: 71%) of white crystals of the derivative 25 is thereby obtained.

Analysis: $C_{14}H_{23}NO_2Si_2$ Calculated: C 57.29; H 7.90; N 4.77. Found: C 57.39; H 7.96; N 4.72.

Example V

Preparation of the compound No. 26 of Table I
5,6-[(1-Ethoxyethylidene)dioxy]indole In a round-bottom flask equipped with a distillation system, 14.6 ml (0.08 mole) of triethyl orthoacetate and 3 g (0.02 mole) of 5,6-dihydroxyindole are heated on an oil bath brought to 120° C., in such a way that the ethanol formed distills continuously (reaction time: 4 hours). The excess triethyl orthoacetate is distilled off and the fraction of boiling point 160° C. at $1.06 \times 10^2$ Pa isolated. The colorless oil obtained crystallizes to give the compound 26 (2.71 g; yield: 62%).

Analysis: $C_{12}H_{13}NO_3$ Calculated: C 65.74; H 5.98; N 6.39. Found: C 65.34; H 6.01; N 6.29.

Example VI

Preparation of the compound No. 24 of Table I
5-Hydroxy-6-(trimethylsilyloxy)indole and
6-hydroxy-5-(trimethylsilyloxy)indole A solution of 200 ml of dry tetrahydrofuran (THF) containing 3 g (0.02 mole) of 5,6-dihydroxyindole and 8.2 g (0.04 mole) of bis(trimethylsilyl)urea is stirred for 2 and a half hours. After the addition of 100 ml of toluene, the organic phase is washed with water, and it is concentrated under vacuum after being dried over sodium sulphate. The 5 g of residue are passed rapidly through a silica column (eluent: $CH_2Cl_2$). As well as the disilyl derivative 25, 0.5 g of the derivative 24 (yield: 11%), a 30:70 mixture of the two monosilyl derivatives as shown by the proton NMR spectrum, is recovered.

Analysis: $C_{11}H_{15}NO_2Si$ Calculated: C 59.69; H 6.83; N 6.33 Found: C 59.27; H 6.86; N 6.33

Example VII

Preparation of the compound No. 27 of Table I
(5,6-Dihydroxyindole cyclic phosphodiester)

6.06 g (0.06 mole) of triethylamine are added in the course of 15 minutes at room temperature, under nitrogen and in the absence of moisture, to a solution of 4.14 g (0.06 mole) of 1,2,4-triazole and 1.84 ml (0.02 mole) of phosphorus oxychloride in 150 ml of dry dioxane. The mixture is left with stirring for 40 minutes at 20° C. The triethylamine hydrochloride formed is filtered off, avoiding contact between the filtrate and the air. The solution of phosphoryltris(1,2,4-triazole) obtained is added in the course of 2 hours at 20° C. under nitrogen to a solution of 2.68 g (0.018 mole) of 5,6-dihydroxyindole. The mixture is then stirred for 3 and a half hours and left standing overnight, and the precipitate obtained (2.9 g dry) is filtered off. This precipitate is stirred for 1 hour at room temperature in 100 ml of water, filtered off again and dried. The derivative 27 is recovered (1 g; yield: 26%).

The NMR spectrum is in agreement with the expected structure.

Example VIII

Preparation of the compound in No. 28 of Table I
(5,6-Thiocarbonyldioxyindole)

A solution of 2.82 g (0.0158 mole) of thiocarbonyldiimidazole in 400 ml of toluene is added dropwise at 60° C. and under nitrogen to a solution of 1.49 g (0.01 mole) of 5,6-dihydroxyindole in 100 ml of isopropylether and 50 ml of toluene. The mixture is left with stirring for 2 hours at 60° C. The reaction mixture is concentrated under vacuum. 200 ml of water are added to the residue obtained. The pale yellow precipitate is filtered off and washed copiously with water. It is redissolved in 50 ml of acetone and reprecipitated with 300 ml of water. After drying under a vacuum of 13.3 Pa, 1.2 g (yield: 63%) of the derivative 28 (yellow-tinged powder) are obtained.

Analysis: $C_9H_5NO_2S$ Calculated: C 56.56; H 2.64; N 7.33; S 16.77 Found: C 56.57; H 2.58; N 7.19; S 16.64

Example IX

Preparation of the compound No. 20 of Table I
(6-Benzyloxy-5-butoxyindole)

A mixture of 5-butoxy-4-hydroxy-2-nitrobenzaldehyde (31 g; 0.13 mole), benzylchloride (20.2 g; 0.16 mole) and potassium carbonate (22.11 g; 0.16 mole) in 80 ml of dimethylformamide is heated for 2 hours under reflux with stirring. The reaction mixture is poured into 200 ml of ice-cold water and the precipitate filtered off. After recrystallization in a hexane/toluene mixture, 4-benzyloxy-5-butoxy-2-nitrobenzaldehyde (30.2 g; 71% yield; yellow powder) is obtained; melting point 94° C.

Nitromethane (10.1 ml; 0.185 mole) is added to a mixture of the above derivative (26.3 g; 0.08 mole) in 90 ml of glacial acetic acid and dry ammonium acetate (8.85 g; 0.115 mole). After 5 hours' refluxing, the reaction mixture is poured into 200 ml of ice-cold water. The brown precipitate is filtered off and recrystallized in ethanol. 4-Benzyloxy-5-butoxy-2,8-dinitrostyrene (18.4 g; 62% yield; yellow powder) is obtained; melting point 152° C.

A solution of 160 ml of absolute ethanol and 80 ml of acetic acid is brought to 60° C. To this solution, activated iron (48 g) is added; the mixture is brought to 80°–85° C. with thorough stirring and the derivative obtained above (8.9 g; 0.024 mole) is added in the course 15 minutes. After 30 minutes' stirring at 85° C., the ferric sludge is filtered off and rinsed with 300 ml of acetic acid followed by 300 ml of ethanol. The filtrate is diluted with ice. The precipitate formed is filtered off, washed with water and dried. After passage through a column of silica 60 (eluent: $CH_2Cl_2$), the derivative 20 is recovered (5 g; 70% yield).

Analysis: $C_{19}H_{21}NO_2$ Calculated: C 77.26; H 7.16; N 4.74. Found: C 77.36; H 7.17; N, 4.72.

Example X

Preparation of the compound No. 21 of Table I
(5-Butoxy-6-hydroxyindole)

The above derivative 20 (4 g; 0.0135 mole) was hydrogenated under 50 atmospheres of hydrogen in a bomb with 40 ml of ethanol and 0.6 g of palladinized charcoal (10% palladium) for 3 hours. After filtration and evaporation of the solvent the residue was recrystallized in a benzene/hexane mixture to give the derivative 21 (2.5 g; 90% yield.

Analysis: $C_{12}H_{15}NO_2$ Calculated: C 70.22; H 7.37; N 6.82. Found: C 70.31; H 7.28; N, 6.77.

Example XI

Preparation of the compound No. 22 of Table I
(5-Benzyloxy-6-butoxyindole)

8.6 g of activated iron are added at 60° C. to a solution of 28 ml of absolute ethanol and 14 ml of acetic acid. The mixture is kept for 15 minutes at 80° C. and 5-benzyloxy-4-butoxy-2,β-dinitrostyrene (1.6 g; 0.0043 mole) is added. The mixture is left at 80° C. for 1 hour, and the ferric sludge is filtered off and rinsed with 40 ml of ethanol and 40 ml of acetic acid. The filtrate is diluted with 100 ml of ice-cold water. After extraction of the solution with methylene chloride and drying of the organic phase over sodium sulphate, the organic phase is concentrated and chromatographed on silica 60 (eluent: toluene/$CH_2Cl_2$, 50:50). 0.5 g (40% yield) of the derivative 22 is obtained.

Analysis: $C_{19}H_{21}NO_2$ Calculated: C 77.26; H 7.16; N 4.74. Found: C 77.06; H 7.14; N 4.82.

Example XII

Preparation of the compound No. 23 of Table I
(6-Butoxy-5-hydroxyindole)

The above derivative 22 (0.5 g; 0.0017 mole) was hydrogenated under 50 atmospheres of hydrogen in a bomb with 5 ml of absolute ethanol and 70 mg of pallidinized charcoal (10% palladium) for 2 hours. After filtration and evaporation of the solvent, the residue was purified by chromatography on silica 60 (eluent: $CH_2Cl_2$) to give the derivative 23 (0.19 g; beige powder; 55% yield).

Analysis: $C_{12}H_{15}NO_2$ Calculated: C 70.22; H 7.37; N 6.82. Found: C 70.11; H 7.37; N, 6.75.

Example XIII

Preparation of the compound No. 29 of Table I
(5-Methoxy-6-trimethylsilyloxyindole)

The derivative 4 (2.04 g; 0.0125 mole) and N,O-bis(-trimethylsilyl)acetamide (5.08 g; 0.025 mole) are mixed at room temperature until solubilization is complete. After chromatography on a column of silica 60 (eluent: $CH_2Cl_2$), the derivative 29 is obtained (2.54 g; 86% yield).

Analysis: $C_{12}H_{17}NO_2Si$ Calculated: C 61.24; H 7.28; N 5.95. Found: C 61.30; H 7.32; N 6.01.

Example XIV

Preparation of the compound No. 30 of Table I
[5,6-Bis(trimethylsilyloxy)-2-methylindole]

The derivative 14 (90 mg; $5.5 \times 10^{-4}$ mole) and N,O-bis(trimethylsilyl)acetamide (220 mg; $1.1 \times 10^{-3}$ mole) are stirred at room temperature until solubilization is complete. The product obtained is purified on a column of silica 60 (eluent: toluene/$CH_2Cl_2$, 50:50). The derivative 30 is obtained (0.14 g; 83% yield).

Analysis: $C_{15}H_{25}NO_2Si_2$ Calculated: C 58.58; H 8.19; N 4.55. Found: C 58.54; H 8.16; N 4.60.

Example XV

Preparation of the compound No. 31 of Table I
(5,6-Carbonyldioxy-2-methylindole)

Carbonyldiimidazole (1.67 g; 0.0103 mole) dissolved in 300 ml of toluene is added under reflux to the derivative 14 (0.51 g; 0.0031 mole) dissolved in 50 ml of isopropyl ether. After 2 hours under reflux, 200 ml of water are added and the toluene phase is separated and then dried over sodium sulphate. The solvent is evaporated off and the product recrystallized in a 50:50 mixture of water and ethanol. The derivative 31 is obtained (0.45 g; 76% yield).

Analysis: $C_{10}H_7NO_3$ Calculated: C 63.49; H 3.73; N 7.40. Found: C 63.44; H 3.75; N 7.06.

Examples XVI and XVII

Preparation of the compounds Nos. 32 and 33 of Table I [(5 or 6)-Hydroxy-(6 or 5)-myristoyloxyindole and 5,6-dimyristoyloxyindole]

A solution of 5,6-dihydroxyindole (2.98 g; 0.02 mole) in 300 ml of THF and N-myristoylimidazole (5.57 g; 0.02 mole) is brought to reflux for 4 hours. After concentration under vacuum, the residue is chromatographed on a column of silica 60 (eluent: $CH_2Cl_2$) to give the compound 33 (2.6 g; 23% yield);

Analysis: $C_{36}H_{59}NO_4$ Calculated: C 75.88; H 10.44; N 2.46; Found: C 75.60; H 10.40; N 2.71;

and the compound 32 (2.7 g; 38% yield), which is a 70:30 mixture of the monoesters, as shown by the proton NMR spectrum.

Analysis: $C_{22}H_{33}NO_3$ Calculated: C 73.50; H 9.25; N 3.90. Found: C 73.59; H 9.25; N 3.87.

Examples XVIII and XIX

Preparation of the compounds Nos. 34 and 35 of Table I [(5 or 6)Hydroxy-(6 or 5)-oleoyloxyindole and 5,6-dioleoyloxyindole]

N-oleoylimidazole dissolved in 100 ml of tetrahydrofuran is added dropwise at 20° C. under nitrogen to a solution of 5,6-dihydroxyindole (2.98 g; 0.02 mole) in 50 ml of tetrahydrofuran. The mixture is brought to reflux for 4 hours. The solvent is removed under vacuum and the residue chromatographed on silica 60 (eluent: toluene/$CH_2Cl_2$, 50:50) to give the compound 35 (1.9 g; 14% yield);

Analysis: $C_{44}H_{71}NO_4$ Calculated: C 77.94; H 10.55; N 2.06; Found: C 77.84; H 10.34; N 2.11;

and the compound 34 (eluent: $CH_2Cl_2$) (5 g; 60% yield), which is a 70:30 mixture of the two monoesters, as shown by the proton NMR spectrum.

Analysis: $C_{26}H_{39}NO_3$ Calculated: C 75.50; H 9.50; N 3.39. Found: C 75.62; H 9.54; N 3.41.

Example XX

Preparation of the compound No. 36 of Table I [5,6-Bis(trimethylsilyloxy)-2-carbethoxyindole]

The derivative 11 (442 mg; 0.002 mole) and N,O-bis(-trimethylsilyl)acetamide (814 mg; 0.004 mole) are stirred at 40° C. for 30 minutes. The solution obtained is chromatographed on silica 60 (eluent: toluene/$CH_2Cl_2$, 50:50). After concentration under vacuum, the derivative 36 is obtained (0.59 g; 73% yield).

Analysis: $C_{17}H_{27}NO_4Si_2$ Calculated: C 55.85; H 7.44; N 3.83. Found: C 55.90; H 7.55; N 3.77.

Example XXI

Preparation of the compound No. 37 of Table I [5,6-Bis(trimethylsilyloxy)-2-(trimethylsilyloxycarbonyl)indole]

The derivative 12 (0.2 g; 0.00103 mole) and N,O-bis(-trimethylsilyl)acetamide (2.5 g; 0.0124 mole) are brought to 60° C. for 1 hour with stirring. The solution is poured into 50 g of ice and the precipitate filtered off and washed with water. It is taken up in dichloromethane and dried over sodium sulphate. After evaporation under vacuum, the derivative 37 is obtained (0.35 g; 83% yield). MS (70 eV) for $C_{18}H_{31}NO_4Si_3$: 409 ($M^+$, 12.5), 337(41), 319(14), 232(30), 75(75) and 73(100).

Example XXII

Preparation of the compound No. 38 of Table I [5,6-Bis(trimethylsilyloxy)-3-methylindole]

The derivative 16 (0.3 g; 0.0018 mole) and N,O-bis(-trimethylsilyl)acetamide (0.61 g; 0.0036 mole) are stirred for 30 minutes at room temperature. The solution obtained is chromatographed on silica 60 (eluent: $CH_2Cl_2$) to give the derivative 38 (0.43 g; 78% yield).

Analysis: $C_{15}H_{25}NO_2Si_2$ Calculated: C 58.57; H 8.19; N 4.55. Found: C 58.55; H 8.18; N 4.53.

Example XXIII

Preparation of the compound No. 39 of Table I (6-Hexadecyloxy-5-methoxyindole)

The derivative 4 (2 g; 0.0123 mole) dissolved in 10 ml of dimethylformamide (DMF) is introduced dropwise in the course of 20 minutes into a mixture of 1-bromohexadecane (4.5 g; 0.0148 mole) and potassium carbonate (1.87 g; 0.0125 mole) in 45 ml of DMF at 70° C. and under nitrogen. The reaction mixture is stirred under nitrogen at 80° C. for 3 and a half hours. The blackish mixture is poured into ice-cold water with stirring and the brownish solid form is immediately filtered off and washed with water. It is taken up in dichloromethane and dried over sodium sulphate. After chromatography on silica 60 (eluent: toluene/$CH_2Cl_2$, 50:50), and recrystallization in hexane, the derivative 39 is obtained (1.66 g; 35% yield).

Analysis: $C_{25}H_{41}NO_2$ Calculated: C 77.47; H 10.66; N 3.61. Found: C 77.35; H 10.62; N 3.71.

Examples XXIV and XXV

Preparation of the compounds Nos. 40 and 41 of Table I (6-Hexadecyloxy-5-hydroxyindole and 5-hexadecyloxy-6-hydroxyindole)

Potassium carbonate (2.76 g; 0.02 mole), 5,6-dihydroxyindole (3 g; 0.02 mole) and 1-bromohexadecane (6.14 g; 0.02 mole) are introduced successively, at 50° C., under nitrogen and with stirring, into 30 ml of dry DMF. The mixture is heated to 60°-70° C. for 2 and a half hours. The blackish mixture is poured into ice-cold water with brisk stirring and the dark brown precipitate is immediately filtered off, washed with water, taken up with dichloromethane and dried for 5 minutes over sodium sulphate. The solution is concentrated and chromatographed on silica 60 (eluent: toluene/$CH_2Cl_2$, 50:50) to give, in fractions 14 to 18, the compound 40 (1.8 g; 24% yield);

Analysis: $C_{24}H_{39}NO_2$ Calculated: C 77.16; H 10.52; N 3.75; Found: C 77.44; H 10.54; N 3.85;

and, in fractions 23 to 33, the compound 41 (0.8 g; 11% yield).

Analysis: $C_{24}H_{39}NO_2$ Calculated: C 77.16; H 10.52; N 3.75. Found: C 77.07; H 10.59; N 3.91.

Examples XXVI and XXVII

Preparation of the compounds Nos. 42 and 43 of Table I [5,6-Dipivaloyloxyindole and (5 or 6)-hydroxy-(6 or 5)-pivaloyloxyindole]

N,N'-carbonyldiimidazole (1.78 g; 0.011 mole) is added to a solution of pivalic acid (1.122 g; 0.011 mole) in 25 ml of methylene chloride. The mixture is left with stirring at room temperature until the evolution of $CO_2$ gas ceases (1 hour). 5,6-Dihydroxyindole (1.64 g; 0.011 mole) is added under nitrogen and at room temperature, and the mixture is left with stirring for 4 hours. The organic phase is washed with water and dried over sodium sulphate. After separation on a chromatographic column of silica 60, the derivative 42 is obtained (eluent: toluene/CH$_2$Cl$_2$, 50:50) (0.59 g; 17% yield);

Analysis: C$_{18}$H$_{23}$NO$_4$ Calculated: C 68.12; H 7.30; N 4.41; Found: C 68.02; H 7.27; N 4.49;

and the derivative 43 (eluent: CH$_2$Cl$_2$) (1.74 g; 68% yield).

Analysis: C$_{13}$H$_{15}$NO$_3$ Calculated: C 66.94; H 6.48; N 6.00. Found: C 66.77; H 6.49; N 5.90.

Examples XXVIII and XXIX

Preparation of the compounds Nos. 44 and 45 of Table I [5,6-Dihexanoyloxyindole and (5 or 6)-hexanoyloxy-(6 or 5)-hydroxyindole]

In a manner identical to the previous examples, hexanoic acid (2.65 g; 0.022 mole) was treated in methylene chloride (50 ml) with N,N'-carbonyldiimidazole (3.75 g; 0.022 mole) and 5,6-dihydroxyindole (3.28 g; 0.022 mole). There are obtained the derivative 44 (1.90 g; 25% yield);

Analysis: C$_{20}$H$_{27}$NO$_4$ Calculated: C 69.54; H 7.89; N 4.05; Found: C 69.26; H 7.93; N 3.96;

and the derivative 45 (3.21 g; 59% yield).

Analysis: C$_{14}$H$_{17}$NO$_3$ Calculated: C 68.00; H 6.93; N 5.66. Found: C 67.65; H 6.98; N 5.64.

Examples XXX and XXXI

Preparation of the compounds Nos. 46 and 57 of Table I [5,6-Dibutanoyloxyindole and (5 or 6)-butanoyloxy-(6 or 5)-hydroxyindole]

In a manner identical to the previous Examples, butanoic acid (2.9 g; 0.033 mole) was treated in methylene chloride (75 ml) with N,N'-carbonyldiimidazole (5.35 g; 0.033 mole) and 5,6-dihydroxyindole (4.92 g; 0.033 mole). There are obtained the derivative 46 (2.77 g; 29% yield);

Analysis: C$_{16}$H$_{19}$NO$_4$ Calculated: C 66.42; H 6.62; N 4.84; Found: C 66.65; H 6.64; N 4.76;

and the derivative 47 (2.64 g; 36.5% yield).

Analysis: C$_{12}$H$_{13}$NO$_3$ Calculated: C 65.74; H 5.98; N 6.39. Found: C 65.46; H 5.94; N 6.14.

Composition Example 1

The following composition is prepared:

| | |
|---|---|
| Compound 4 | 0.75 g |
| Oleyl/cetyl alcohol containing 30 moles of ethylene oxide | 7.0 g |
| Stearyl alcohol | 4.0 g |
| Isopropyl myristate | 4.0 g |
| Liquid paraffin | 11.0 g |
| Silicone oil | 1.0 g |
| Propylene glycol | 5.0 g |
| Sorbitol in 70% strength aqueous solution | 10.0 g |
| Preservatives, perfumes qs | |
| Demineralized water qs | 100 g |

This composition takes the form of a milk. When applied on the skin, it enables a grey-brown coloring resembling the natural pigmentation to be obtained after exposure to sunlight.

Composition Example 2

The following oily composition is prepared:

| | |
|---|---|
| Compound 25 | 0.15 g |
| Ethylene glycol monobutyl ether | 10.0 g |
| Isopropyl myristate | 20.0 g |
| Sunflower oil | 11.0 g |
| Silicone oil qs | 100 g |

After application of this oily composition on the skin, followed by exposure to sunlight, a brownish coloring is obtained.

Composition Example 3

The following composition is prepared:

| | |
|---|---|
| Compound 25 | 0.1 g |
| Hydrocarbon mineral wax sold under the name OZECIRE 310 S by CIRES ET DERIVES | 15.0 g |
| Beeswax | 6.0 g |
| Ricinoleic acid triglycerides | 15.0 g |
| Oleyl alcohol | 12.0 g |
| Hydrogenated lanolin sold under the name HYDROLAN H by ONYX | 8.0 g |
| Liquid lanolin sold under the name ARGONOL 60 by WESTBROOK | 7.0 g |
| Carnauba wax | 1.5 g |
| Hydrogenated and interesterified triglycerides (palm and copra origin) sold under the name LIPOCIRE A by GATTEFOSSE | 5.0 g |
| Di-tert-butyl-para-cresol | 0.1 g |
| Liquid paraffin qs | 100 g |

Sticks may be prepared by means of this composition. Application on the skin, followed by exposure to sunlight, leads to a grey-brown coloring.

Composition Example 4

The following composition is prepared:

| | |
|---|---|
| Compound 4 | 0.5 g |
| Carboxyvinyl polymer sold under the name CARBOPOL 940 by GOODRICH | 0.4 g |
| Propylene glycol | 5.0 g |
| Isoporopyl myristate | 3.0 g |
| Mixture of glycerol mono- and distearates sold under the name GELEOL by GATTEFOSSE | 2.0 g |
| Ethyl alcohol | 20.0 g |
| Triethanolamine | 0.6 g |
| Preservative qs | |
| Demineralized water qs | 100 g |

This composition takes the form of an opaque gel. Application on the skin and exposure to sunlight leads to a grey-brown coloring.

Composition Example 5

The following composition is prepared:

| | |
|---|---|
| Compound 4 | 0.9 g |
| Sorbitol in 70% strength aqueous solution | 5.0 g |
| Mixture of glycerol mono- and distearates sold under the name GELEOL by GATTEFOSSE | 2.0 g |
| Myristyl alcohol | 6.0 g |
| Oleyl alcohol containing 20 moles of ethylene oxide | 10.0 g |
| Isopropyl myristate | 4.0 g |
| Silicone oil | 1.0 g |
| Sunflower oil | 12.0 g |
| Preservative, perfumes qs | |
| Demineralized water qs | 100 g |

This composition is a cream. Application on the skin, followed by exposure to sunlight, enables a grey-brown coloring to be obtained which is similar to the pigmentation resulting from natural tanning.

Composition Example 6

The following composition is prepared:

| | |
|---|---|
| Compound 8 | 0.1 g |
| Propylene glycol | 5.0 g |
| Ethyl alcohol | 5.0 g |
| Hydroxyethylcellulose sold under the name CELLOSIZE PCG10 by UNION CARBIDE | 1.5 g |
| Demineralized water qs | 100 g |

This composition takes the form of a gel. Application on the skin, followed by exposure to sunlight, enables a grey-brown coloring to be obtained.

What is claimed:

1. A cosmetic composition for imparting to the skin a coloring which is substantially similar to the pigmentation resulting from natural tanning, said composition comprising, in a cosmetically acceptable medium suitable for topical application to the skin, a compound of the formula

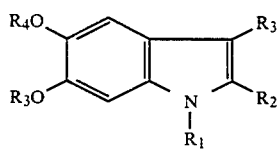

wherein
$R_1$ represents hydrogen, lower alkyl having 1-6 carbon atoms or $-SiR_9R_{10}R_{11}$,
$R_2$ and $R_3$, each independently, represent hydrogen, lower alkyl having 1-6 carbon atoms, carboxyl, lower alkoxy carbonyl wherein the alkoxy moiety has 1-6 carbon atoms or $-COOSiR_9R_{10}R_{11}$,
$R_4$ and $R_5$, each independently, represent hydrogen, linear or branched $C_1-C_{20}$ alkyl, formyl, linear or branched $C_2-C_{20}$ acyl, linear or branched $C_3-C_{20}$ alkenoyl, $R_6OSO_2-$, $-SiR_9R_{10}R_{11}$, $-P(O)(OR_6)_2$ or aralkyl, or alternatively,
$R_4$ and $R_5$, together with the oxygen atoms to which they are attached, form a ring optionally containing a carbonyl group when at least one of $R_1$, $R_2$ or $R_3$ is other than hydrogen or alternatively a thiocarbonyl group, $>P(O)OR_6$, $>CR_7R_8$ or methylene,
$R_6$ represents hydrogen or lower alkyl having 1-6 carbon atoms,
$R_7$ represents hydrogen or lower alkyl having 1-6 carbon atoms,
$R_8$ represents lower alkoxy having 1-6 carbon atoms or mono- or dialkylamino, and
$R_9$, $R_{10}$, and $R_{11}$, each independently, represent linear or branched lower alkyl having 1-6 carbon atoms,
with the proviso that at least one of $R_1$, $R_2$, $R_3$, $R_4$ and $R_5$, is other than hydrogen and
with the further proviso that when $R_1$ represents hydrogen, $R_2$ and $R_3$, each independently, represent hydrogen or lower alkyl having 1-6 carbon atoms and (1) at least one of $R_4$ and $R_5$ represents linear or branched $C_1-C_{20}$ alkyl, linear or branched $C_2-C_{20}$ acyl or linear or branched $C_3-C_{20}$ alkenoyl with the other of $R_4$ and $R_5$ being hydrogen, or (2) $R_4$ and $R_5$, simultaneously, represent $-SiR_9R_{10}R_{11}$ wherein $R_9$, $R_{10}$ and $R_{11}$ have the meanings given above,
and with the further proviso that when $R_4$ and $R_5$ are simultaneously hydrogen, $R_1$ is other than lower alkyl and that when $R_2$ is carboxyl, $R_4$ and $R_5$ are not simultaneously linear or branched, $C_1-C_{20}$ alkyl,
and the corresponding salt with an alkali metal, an alkaline earth metal, ammonium or an amine.

2. A cosmetic composition for imparting to the skin a coloring which is substantially similar to the pigmentation resulting from natural tanning, said composition comprising, in a cosmetically acceptable medium suitable for topical application to the skin, a compound selected from the group consisting of
5,6-dibenzyloxyindole,
5-benzyloxy-6-methoxyindole,
6-benzyloxy-5-methoxyindole,
6-hydroxy-5-methoxyindole,
5-hydroxy-6-methoxyindole,
5,6-diacetoxyindole,
6-acetoxy-5-methoxyindole,
(5 or 6)-acetoxy-(6 or 5)-hydroxyindole,
5,6-dibenzyloxy-2-carbethoxyindole,
5,6-dibenzyloxy-2-carboxyindole,
5,6-dihydroxy-2-carbethoxyindole,
5,6-dihydroxy-2-carboxyindole,
5,6-dibenzyloxy-2-methylindole,
5,6-dibenzyloxy-3-methylindole,
(5 or 6)-formyloxy-(6 or 5)-hydroxyindole,
(5 or 6)-acetoxy-(6 or 5)-formyloxyindole,
6-formyloxy-5-methoxyindole,
6-benzyloxy-5-butoxyindole,
5-butoxy-6-hydroxyindole,
5-benzyloxy-6-butoxyindole,
6-butoxy-5-hydroxyindole,
(5 or 6)-hydroxy-(6 or 5)-trimethylsilyloxy-indole,
5,6-bis (trimethylsilyloxy) indole,
5,6-[(1-ethoxyethylidene)-dioxy]indole,
5,6-dihydroxyindole cyclic-phosphodiester,
5,6-thiocarbonyl dioxyindole,
5-methoxy-6-trimethylsilyloxyindole,
5,6-bis(trimethylsilyloxy)-2-methylindole,
5,6-carbonyldioxy-2-methylindole,
(5 or 6)-hydroxy-(6 or 5)-myristoyloxyindole,
5,6-dimyristoyloxyindole,
(5 or 6)-hydroxy-(6 or 5)-oleoyloxyindole,
5,6-dioleoyloxyindole,
5,6-bis(trimethylsilyloxy)-2-carbethoxyindole,
5,6-bis(trimethylsilyloxy)-2-(trimethyl-silyloxycarbonyl)indole,
5,6-bis(trimethylsilyloxy)-3-methylindole,
6-hexadecyloxy-5-methoxyindole,
6-hexadecyloxy-5-hydroxyindole,
5-hexadecyloxy-6-hydroxyindole,
5,6-dipivaloyloxyindole,
(5 or 6)-hydroxy-(6 or 5)-pivaloyloxyindole,
5,6-dihexanoyloxyindole,
(5 or 6)-hexanoyloxy-(6 or 5)hydroxyindole,
5,6-dibutanoyloxyindole and
(5 or 6)-butanoyloxy-(6 or 5)-hydroxyindole.

3. A cosmetic composition for imparting to the skin a coloring which is substantially similar to the pigmentation resulting from natural tanning, said composition comprising, in a cosmetically acceptable medium suitable for topical application to the skin, a compound of the formula

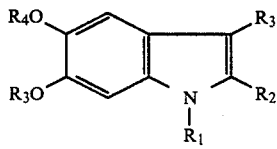

wherein $R_1$ represents hydrogen, or $-SiR_9R_{10}R_{11}$, $R_2$ and $R_3$, each independently, represent hydrogen, lower alkyl having 1–6 carbon atoms, lower alkoxy carbonyl wherein the alkoxy moiety has 1–6 carbon atoms or $-COOSiR_9R_{10}R_{11}$, $R_4$ and $R_5$, each independently, represent hydrogen, linear or branched $C_1-C_{20}$ alkyl, formyl, linear or branched $C_2-C_{20}$ acyl, linear or branched $C_3-C_{20}$ alkenoyl, $R_6OSO_2-$, $-SiR_9R_{10}R_{11}$, $-P(O)(OR_6)_2$ or aralkyl, or alternatively, $R_4$ and $R_5$, together with the oxygen atoms to which they are attached, form a ring optionally containing a carbonyl group when at least one of $R_1$, $R_2$ or $R_3$ is other than hydrogen or alternatively a thiocarbonyl group, $>P(O)OR_6$, $>CR_7R_8$ or methylene, $R_6$ represents hydrogen or lower alkyl having 1–6 carbon atoms, $R_7$ represents hydrogen or lower alkyl having 1–6 carbon atoms, $R_8$ represents lower alkoxy having 1–6 carbon atoms or mono- or dialkylamino, and $R_9$, $R_{10}$, and $R_{11}$, each independently, represent linear or branched lower alkyl having 1–6 carbon atoms, with the proviso that at least one of $R_1$, $R_2$, $R_3$, $R_4$ and $R_5$, is other than hydrogen and with the further proviso that when $R_1$ represents hydrogen, $R_2$ and $R_3$, each independently, represent hydrogen or lower alkyl having 1–6 carbon atoms and (1) at least one of $R_4$ and $R_5$ represents linear or branched $C_1-C_{20}$ alkyl, linear or branched $C_2-C_{20}$ acyl or linear or branched $C_3-C_{20}$ alkenoyl with the other of $R_4$ and $R_5$ being hydrogen, or (2) $R_4$ and $R_5$, simultaneously, represent $-SiR_9R_{10}R_{11}$ wherein $R_9$, $R_{10}$ and $R_{11}$ have the meanings given above, and the corresponding salt with an alkali metal, an alkaline earth metal, ammonium or an amine.

4. The cosmetic composition of claim 1, wherein said cosmetically acceptable medium is an anhydrous medium containing less than 1% water.

5. The cosmetic composition of claim 1, wherein said cosmetically acceptable medium contains a solvent selected from the group consisting of a $C_1-C_4$ lower alcohol, ethylene glycol, propylene glycol, dipropylene glycol, tripropylene glycol, ethylene glycol monomethyl ether, ethylene glycol monoethyl ether, ethylene glycol monobutyl ether and ethylene glycol monoethyl ether acetate.

6. The cosmetic composition of claim 1, wherein said cosmetically acceptable medium contains or consists exclusively of fats.

7. The cosmetic composition of claim 1, in the form of a lotion, gel, emulsion, balm, stick, oil, milk or cream.

8. The cosmetic composition of claim 1, which also includes at least one of a thickener, a demulcent, a humectant, a superfatting agent, a sequestering agent, an emollient, a wetting agent, a surfactant, a polymer, a preservative, an antifoaming agent, a perfume, an emulsifier, and a bactericide.

9. The cosmetic composition of claim 1, which also includes a sunscreen which is specific for UV-B radiation or UV-A radiation or both, said sunscreen being compatible with the compound of formula I.

10. The cosmetic composition of claim 1, wherein said compound of formula I is present in an amount ranging from 0.01 to 15 percent by weight relative to the total weight of said composition.

11. A process for coloring the skin in order to impart thereto a coloring which is substantially similar to the pigmentation resulting from natural tanning, said process comprising applying to the skin in an effective amount to color the skin a cosmetic composition comprising, in a cosmetically acceptable medium suitable for topical application to the skin, a compound of the formula

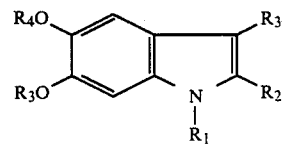

wherein $R_1$ represents hydrogen, lower alkyl having 1–6 carbon atoms or $-SiR_9R_{10}R_{11}$, $R_2$ and $R_3$, each independently, represent hydrogen, lower alkyl having 1–6 carbon atoms, carboxyl, lower alkoxy carbonyl wherein the alkoxy moiety has 1–6 carbon atoms or $-COOSiR_9R_{10}R_{11}$, $R_4$ and $R_5$, each independently, represents hydrogen, linear or branched $C_1-C_{20}$ alkyl, formyl, linear or branched $C_2-C_{20}$ acyl, linear or branched $C_3-C_{20}$ alkenoyl, $R_6OSO_2-$, $-SiR_9R_{10}R_{11}$, $-P(O)(OR_6)_2$ or aralkyl, or alternatively, $R_4$ and $R_5$, together with the oxygen atoms to which they are attached, form a ring optionally containing a carbonyl group when at least one of $R_1$, $R_2$ or $R_3$ is other than hydrogen or alternatively a thiocarbonyl group, $>P(O)OR_6$, $>CR_7R_8$ or methylene, $R_6$ represents hydrogen or lower alkyl having 1–6 carbon atoms, $R_7$ represents hydrogen or lower alkyl having 1–6 carbon atoms, $R_8$ represents lower alkoxy having 1–6 carbon atoms or mono- or dialkylamino, and $R_9$, $R_{10}$, and $R_{11}$, each independently, represent linear or branched lower alkyl having 1–6 carbon atoms, with the proviso that at least one of $R_1$, $R_2$, $R_3$, $R_4$ and $R_5$, is other than hydrogen and with the further proviso that when $R_1$ represents hydrogen, $R_2$ and $R_3$, each independently, represent hydrogen or lower alkyl having 1–6 carbon atoms and (1) at least one of $R_4$ and $R_5$ represents linear or branched $C_1-C_{20}$ alkyl, linear or branched $C_2-C_{20}$ acyl or linear or branched $C_3-C_{20}$ alkenoyl with the other of $R_4$ and $R_5$ being hydrogen or (2) $R_4$ and $R_5$ simultaneously represent $-SiR_9R_{10}R_{11}$ wherein $R_9$, $R_{10}$ and $R_{11}$ have the meanings given above, and the corresponding salt with an alkali metal, an alkaline earth metal, ammonium or an amine.

* * * * *